US006913615B2

(12) United States Patent
Tolkoff et al.

(10) Patent No.: US 6,913,615 B2
(45) Date of Patent: Jul. 5, 2005

(54) CHEMILUMINESCENT TREATMENT OF ACNE

(75) Inventors: Marc Joshua Tolkoff, Brookline, MA (US); Andy Levine, Newton, MA (US)

(73) Assignee: LumeRx, Inc., Boston, MA (US)

( * ) Notice: Subject to any disclaimer, the term of this patent is extended or adjusted under 35 U.S.C. 154(b) by 100 days.

(21) Appl. No.: 10/395,027

(22) Filed: Mar. 21, 2003

(65) Prior Publication Data

US 2004/0013623 A1 Jan. 22, 2004

Related U.S. Application Data

(60) Provisional application No. 60/366,551, filed on Mar. 25, 2002.

(51) Int. Cl.[7] ............................................... A61B 18/18
(52) U.S. Cl. ............................ 607/88; 128/898; 606/9
(58) Field of Search ...................... 606/4, 5, 9; 607/88; 128/898

(56) References Cited

U.S. PATENT DOCUMENTS

| | | | |
|---|---|---|---|
| 3,984,786 A | 10/1976 | Pike | ........................... 331/94.5 |
| 4,814,949 A | * 3/1989 | Elliott | ........................... 362/34 |
| 4,889,129 A | 12/1989 | Dougherty et al. | |
| 4,998,930 A | 3/1991 | Lundahl | |
| 5,104,392 A | 4/1992 | Kittrell et al. | ................. 606/15 |
| 5,334,171 A | 8/1994 | Kaldany | |
| 5,399,583 A | 3/1995 | Levy et al. | |
| 5,405,369 A | 4/1995 | Selman et al. | |
| 5,445,608 A | 8/1995 | Chen et al. | ................... 604/20 |
| RE35,132 E | * 12/1995 | Bay et al. | ...................... 362/34 |
| 5,531,662 A | 7/1996 | Carr | |
| 5,653,683 A | 8/1997 | D'Andrea | |
| 5,671,998 A | 9/1997 | Collet | ......................... 362/101 |
| 5,800,478 A | 9/1998 | Chen et al. | |
| 5,845,640 A | * 12/1998 | Lawandy | .................... 600/473 |
| 5,871,522 A | 2/1999 | Sentilles | |
| 5,876,427 A | 3/1999 | Chen et al. | |
| 5,913,883 A | 6/1999 | Alexander et al. | ............. 607/88 |
| 5,993,378 A | 11/1999 | Lemelson | ................... 600/109 |
| 6,183,773 B1 | 2/2001 | Anderson | |
| 6,335,465 B1 | 1/2002 | Golub | |
| 6,443,978 B1 | 9/2002 | Zharov | ........................ 607/91 |
| 6,464,625 B2 | 10/2002 | Ganz | |
| 6,491,618 B1 | 12/2002 | Ganz | |
| 6,685,331 B1 * | 2/2004 | Rockwell | ..................... 362/34 |

FOREIGN PATENT DOCUMENTS

| | | |
|---|---|---|
| JP | 10-094583 | 4/1998 |
| WO | WO 98/32370 | 7/1998 |
| WO | WO 00/64537 | 11/2000 |

OTHER PUBLICATIONS

Cunliffe et al., "Phototherapy and *acne vulgaris*," *British Journal of Dermatology*, vol. 142, Issue 5 (May 2000), pp. 1–5.

Futsaether et al., "Intracellular pH changes induced in *Propionibacterium acnes* by UVA radiation and blue light," *Journal of Photochemistry and Photobiology*, Issue 31 (1995), pp. 125–131.

(Continued)

*Primary Examiner*—Roy D Gibson
*Assistant Examiner*—Henry M Johnson, III
(74) *Attorney, Agent, or Firm*—Mills & Onello LLP

(57) ABSTRACT

The present invention provides the ability to treat acne with a device that can be worn by a patient for extended time periods. The device can, for example, enable the delivery of light for time periods that are longer than one might want to sit still in front of a stationary light source. The device is a flexible container that may be fitted to parts of the body to be treated. An example of such a flexible container is a mask for the face. The mask covers the face and has a strap to hold it to the face. The mask is located relative to a light source generating light by chemiluminescence. The mask is worn for a period of time needed to provide the desired amount of light energy to the tissue.

22 Claims, 3 Drawing Sheets

OTHER PUBLICATIONS

Hoare, "Handbook of Medical Protozoology," Bailliere, Tindall and Cox, (Nov., 1949), pp. 77–78.

Hongcharu et al., "Topical ALA–Photodynamic Therapy for the Treatment of *Acne Vulgaris,*" *The Journal of Investigative Dermatology*, vol. 115, No. 2 (Aug. 2000), pp. 1–10.

International Preliminary Examination Report for PCT/US03/09097, Mar. 1, 2004, 4 pgs.

International Search Report for PCT/US03/09097, Oct. 28, 2003, 5 pgs.

Kjeldstad et al., "An Action Spectrum for Blue and Near Ultraviolet Inactivation of *Propionibacterium acnes* with Emphasis on a Possible Porphyrin Photosensitization," *Photochemistry and Photobiology*, vol. 43, No. 1 (1986), pp. 67–70.

Kubey et al., "In Vitro Studies on the Microbicidal Effectiveness of a Xenon–Based Ultraviolet Light Device for Continuous Ambulatory Peritoneal Dialysis Connections," *Blood Purification*, vol. 9 (Mar.–Apr. 1991), pp. 102–108.

Lee et al., "Comparative Studies of Porphyrin Production in *Propionbacterium acnes* and *Propionibacterium granvlosum,*" *Journal of Bacteriology*, vol. 133, No. 2 (Feb. 1978), pp. 811–815.

Martinetto et al., "Bactericidal Effects Induced by Laser Irradiation and Haematoporphyrin against Gram–Positive and Gram–Negative Microorganisms," Bioscience Ediprint, Inc., (1986), pp. 335–342.

Millson et al., "Ex–vivo treatment of gastric *Helieobacter* infection by photodynamic therapy," *Journal of Photochemistry and Photobiology B: Biology*, vol. 32 (1996), pp. 59–65.

Millson et al., "The killing of *Helicobacter pylori* by low–power laser light in the presence of a photosensitiser," *Journal of Medical Microbiology*, vol. 44 (1996), pp. 245–252.

Moretti, "Light–based systems shown to be effective in treating active acne," *The BBI Newsletter*, (Mar. 2002), pp. 72–73.

Papageorgiou et al., "Phototherapy with blue (415 nm) and red (660 nm) light in the treatment of *acne vulgaris,*" *British Journal of Dermatology*, vol. 142 (2000), pp. 973–978.

Shalita et al., "Ance PhotoClearing (APC™) Using a Novel, High–Intensity, Enhanced, Narrow–Band, Blue Light Source," *Clinical Application Notes*, vol. 9, No. 1 (2001), pp. 1–4.

Sigurdsson et al., "Phototherapy of *Acne Vulgaris* with Visible Light," *Dermatology*, vol. 194 (1997), pp. 256–260.

Wells et al., "The Science of Life," The Literary Guild, (1929), pp. 1086–1088.

\* cited by examiner

CHEMILUMINESCENT TREATMENT OF ACNE

CROSS REFERENCE TO RELATED APPLICATIONS

This application claims priority to U.S. provisional patent application Ser. No. 60/366,551, filed Mar. 25, 2002. The provisional application Ser. No. 60/366,551 is incorporated by reference herein.

FIELD OF THE INVENTION

The present invention provides for a method and apparatus for the application of specific wavelengths of light to skin tissue for the purpose of treating and healing acne lesions

BACKGROUND OF THE INVENTION

Roughly 45 million people in the US are afflicted by the skin condition acne vulgaris. It is associated with lesions on the skin that are unsightly but can also be painful and leave scars.

The exact etiology of acne remains controversial. Keratinous material initially plugs the duct of a sebaceous gland. Sebum is produced and trapped, thereby enlarging the gland. The *propionibacterium acnes* (*P. acnes*) bacterium, which is a normal part of the skin flora, propagates in the gland due to the sebum buildup. These bacteria are inflammatory and may lead to the formation of the acne pustules.

Treatments typically include topical and systemic therapies. Topical treatments are aimed at removing follicular plugs and cleaning the sebaceous glands. These treatments are useful in treating some minor forms of acne. Oral treatments include antibiotics to suppress the growth of *P. acnes*. However, these treatments have side effects typical of these drugs, such as skin dryness, digestive problems, and the development of antibiotic resistant bacteria.

It is known that the *P. acnes* bacteria produce porphyrins. The particular porphyrin typically produced by *P. acnes* has a peak in absorption at 415 nanometers. Although red light is absorbed less, the light penetrates the skin deeper than other light. Thus, devices often include 660 nanometer light as well. Also, red light has an anti-inflammatory effect on tissue and may therefore aid in improving healing of pustules.

More recently, the use of both blue light (e.g., 415 nm) and red light (e.g., 660 nm) in the treatment of acne has been described. These lights can be applied with and without photo enhancers. These devices typically require high energy light sources to limit the treatment time to a period that is acceptable for a person to sit still. For example, the light sources tend to be high energy fluorescent bulbs and LEDs.

SUMMARY OF THE INVENTION

The present invention provides the ability to treat acne with a device that can be worn by a patient for extended time periods. The device can, for example, enable the delivery of light for time periods that are longer than one might want to sit still in front of a stationary light source. The device is a flexible container that may be fitted to parts of the body to be treated. An example of such a flexible container is a mask for the face. The mask covers the face and has a strap to hold it to the face. The mask is located relative to a light source generating light by chemiluminescence. The mask is worn for a period of time needed to provide the desired amount of light energy to the tissue.

Chemiluminescence is a chemical reaction that emits light. In practice, two chemicals in liquid form are mixed together. In one embodiment, the mask contains a first portion storing a first chemical and a second portion storing a second chemical. The chemicals mix when, for example, the user breaks a breakable barrier (i.e., a separating mechanism) separating the two portions. The resulting chemical reaction emits light of specific wavelength(s) and for certain amounts of time. The chemicals contain both a dye(s) that creates the specific wavelength(s) of light and an energy-releasing reaction species providing the energy required to "pump" the dye molecules to a higher energy state. When the dye molecule naturally relaxes from its higher energy state, a photon of a specific wavelength is released. The proper selection of the chemicals can provide light of a specific wavelength peak, or, by combining multiple chemicals with different dyes, light of multiple peaks can be delivered. In addition, the chemicals providing the energy-supplying reaction can be selected to be a rapid, very energetic reaction or a longer, slower and less energetic reaction. If one desires a low light intensity for a long time, the chemicals are selected for a slow reaction rate. Conversely, for high intensity, the chemicals for a fast reaction are used. The total number of photons delivered depends on the energy produced by the reaction, the efficiency of the reaction in exciting the dye to its higher energy state, and the efficiency in the excited dye molecules returning to their lower energy state. The brightness of the illumination and the duration of the light are dependent on first order chemical reaction kinetics. That is, heating up the chemicals makes the reaction rate faster, approximately twice as fast for a 10 degree centigrade increase in temperature.

In one embodiment, the light source generates light having a wavelength between about 400 nm and about 450 nm. The light source can also generate additional light having a wavelength between about 630 nm and about 690 nm. In yet another embodiment, the light source generates additional light having a wavelength between about 525 nm and 575 nm.

The masks are made to fit various parts of the body that are affected by acne including the face and/or the back. In one embodiment, the mask is made from a flexible material. For the face, eye, nose and mouth holes are provided. The distal part of each mask is opaque to ensure that most of the light is directed to the tissue.

DETAILED DESCRIPTION OF THE DRAWINGS

Figure 1:
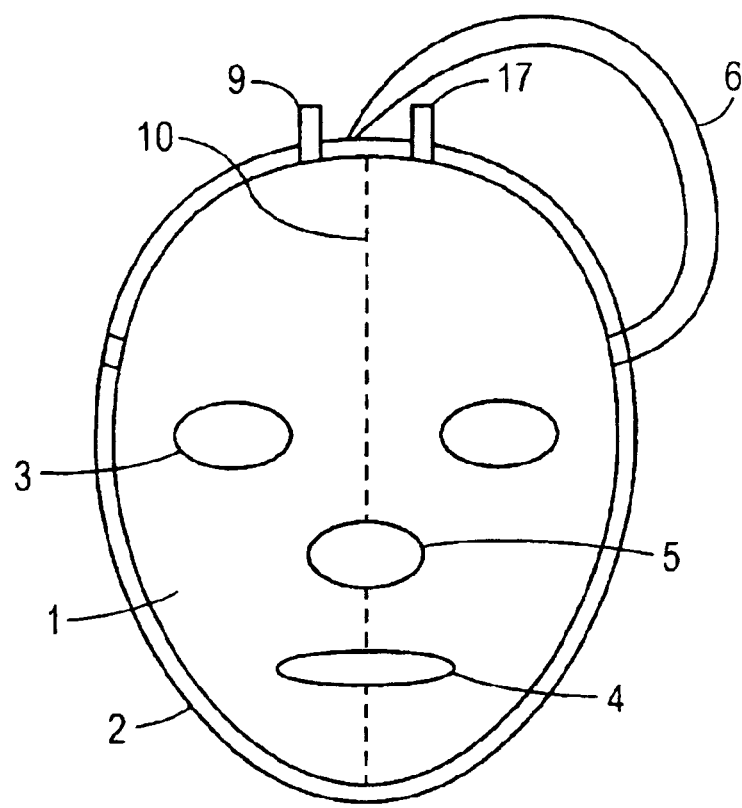
FIG. 1 is a schematic representation of an embodiment of an illuminating face mask.
Figure 2:
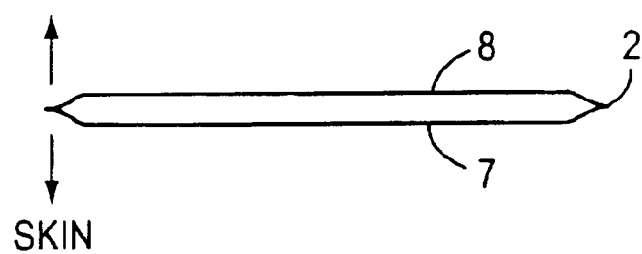
FIG. 2 illustrates an embodiment of a section of the face mask construction.

FIG. 1 illustrates a schematic representation of a mask 1. The mask 1 can have holes for the eyes 3, nose 5 and mouth 4. Alternatively, the mask 1 may have any combination of the holes for the eyes 3, nose 5, and mouth 4 (e.g., holes for the eyes 3 and mouth 4). There is also a strap 6 for holding the mask in place around the head. In one embodiment, the mask 1 includes a fill port 9 that is closed (e.g., by welding or gluing) once the mask is filled. Also referring to FIG. 2, the construction of the mask 1 is such that there is a front sheet 8 and a back sheet 7. The two sheets 7, 8 are joined along their periphery 2 to provide a seal. The sheets may be, for example, welded or glued. Materials may include nylon 6—6, PVC, PET or other translucent polymers. The front sheet 8 can be opaque to light or reflective to reflect the light back towards the back sheet 7 towards the skin to trap the most amount of useful light and direct it to the desired treatment area. The front sheet 8 can be made from opaque or reflective (silver coated) plastics.

Figure 3:
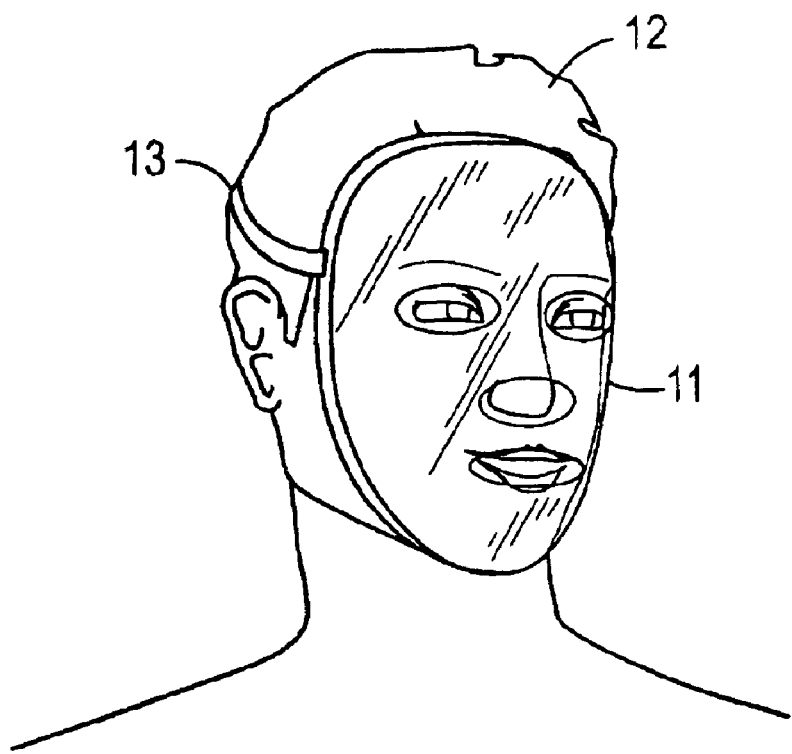
FIG. 3 illustrates an embodiment of a face mask on a person.
Figure 4:
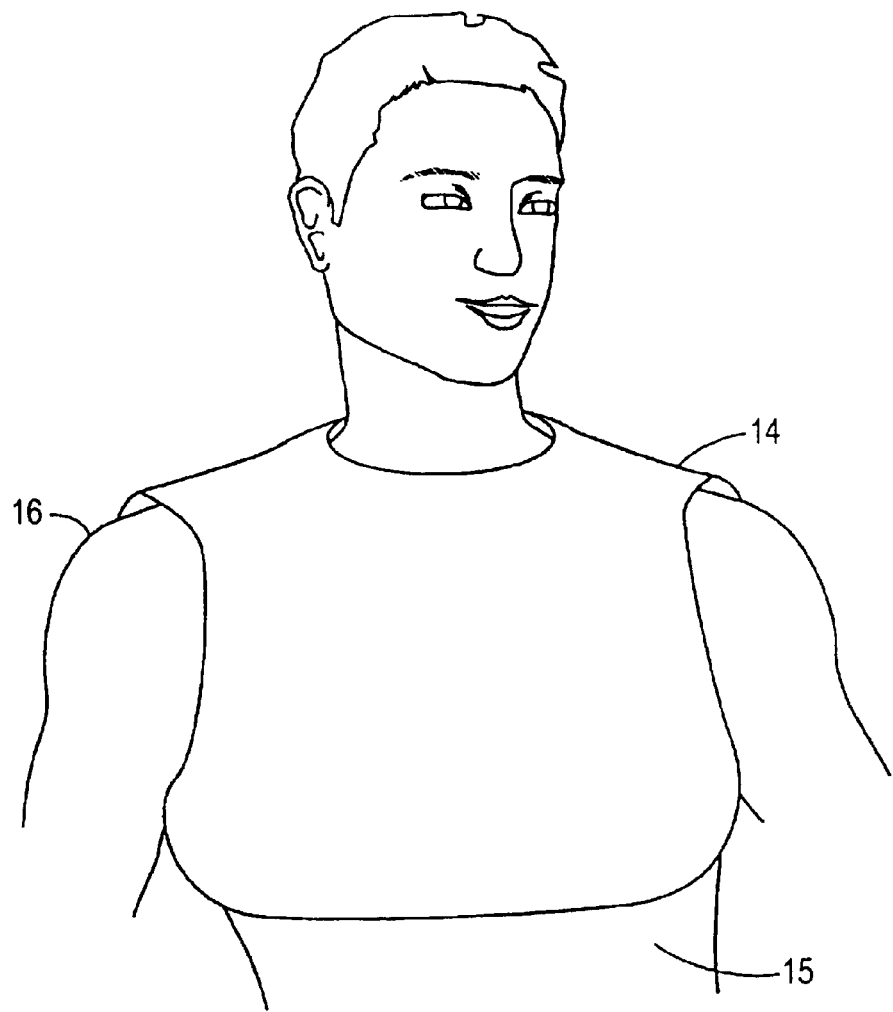
FIG. 4 illustrates an embodiment of a body mask on a person.

Referring to FIG. 3, the face mask 11 is shown in place on the head 12 using the head strap 13. FIG. 4 shows a body mask 14 in place on the upper torso 15. The body mask 14 may cover the front and/or back of the user.

Referring again to FIG. 1, the mask 1 in FIG. 1 is filled with the chemiluminescent solutions through fill ports 9 and 17. The ports 9, 17 are then sealed by, for example, gluing or welding shut. The two solutions are separated in the mask 1 by welding the materials 7 and 8 together along the midline 10 of the mask. In use, the user squeezes the mask, breaking the weld 10 and permitting the solutions to mix.

Alternatively, the mask 1 may be filled with one of the necessary components. A thin glass ampule or plastic package filled with the other solution may be inserted into the mask. The user then breaks the glass ampule or plastic package by squeezing. This releases the activator which mixes with the dye and activates the light source.

The activity of the chemicals is selected to provide blue light with a peak around 415 nm, as this is the wavelength of the peak kill rate of the P. acnes. In other embodiments, the light has a wavelength within a range of 400–450 nm. There is also a peak in the porphyrin absorption around 550 nm so that additionally, we may want to provide chemicals with outputs of 525–575 nm. In some embodiments, chemicals that provide red light around 660 nm (630–690 nm) are applied to reduce inflammation of the tissue. Any or all of these dyes might be included in each device.

The effectiveness of killing P. acnes is dependent on the total amount of energy delivered. In one embodiment, the total amount of energy exposure is between 320 and 430 J/cm2. Further, the energy delivered in these treatments can, for example, range from 4 to 90 mW/cm$^2$. In other embodiments, longer treatments with lower energy exposures is more effective at killing the P. acnes bacteria. The benefit of this invention is that the user may wear the device and continue with daily chores or routines permitting the exposure of large amounts of energy per treatment at low powers or fluxes. Currently available light treatments require the user to sit or lie in front of a light source and therefore interrupts daily activity.

In addition to the light delivery, the mask can also deliver skin softeners or cleansers. The front sheet 7 is impregnated with skin cleansing solutions that transfers to the skin during the treatment.

In yet other embodiments, the mask 1 can be reused a predetermined number of times prior to disposal to, for instance, lower user costs. For example, the mask 1 may contain several compartments of activators, one of which is opened at a time. Another example is that the mask 1 has several glass ampules with activators inside the mask, and one glass ampule is broken at a time. The chemical reaction then proceeds until the activator is used up, but unreacted dye remains to react with the next activator that is exposed when the next glass ampule is broken.

The mask may also have a port through which the solutions can be introduced. Syringes are filled with each of the two solutions, dye and activator. Each component is then injected into the mask and mixed inside the mask. The port has a valve to keep the fluids inside during use. The valve is opened to drain the fluids after use prior to the next use.

Having described certain embodiments of the invention, it will now become apparent to one of skill in the art that other embodiments incorporating the concepts of the invention may be used. Therefore, the invention should not be limited to certain embodiments, but rather should be limited only by the spirit and scope of the following claims.

What is claimed is:

1. A method of treating a skin condition of a patient comprising:
    (a) generating, by chemiluminescence, light having a wavelength between about 400 nm and about 450 nm;
    (b) using an illuminating mask, located relative to the light source, to expose at least a portion of skin of a patient to the light to treat the skin condition of the patient; and
    (c) exposing the skin of the patient to at least one of a skin softener and a cleanser.

2. The method of claim 1 wherein step (a) further comprises
    (a-a) generating additional light having a wavelength between about 630 nm and about 690 nm.

3. The method of claim 1 comprising mixing a first chemical and a second chemical to generate the light.

4. The method of claim 3 wherein the first chemical is stored in a first portion of the mask and the second chemical is stored in a second portion of the mask.

5. The method of claim 3 wherein the mixing of the chemicals to generate light further comprises injecting at least one of the first chemical and the second chemical into the mask through a port located thereon.

6. The method of claim 4 further comprising breaking a separating mechanism which separates the first portion and the second portion to generate the light.

7. The method of claim 1 wherein step (a) further comprises
    (a-a) generating additional light having a wavelength between about 525 nm and about 575 nm.

8. The method of claim 1, wherein the mask is used to treat acne.

9. An apparatus for treating a skin condition of a patient comprising:
    (a) a chemiluminescent light source generating light having a wavelength between about 400 nm and about 450 nm;
    (b) a mask, located relative to the light source, the mask capable of exposing the light to a portion of skin of a patient, the mask having a front side and a back side; and
    (c) a source of at least one of a skin softener and a cleanser connected to the back side, whereby the at least one of a skin softener and a cleanser can transfer to the skin of the patient.

10. The apparatus of claim 9 wherein the light source is located within the mask.

11. The apparatus of claim 9 wherein the mask comprises:
    (b-a) a first portion containing a first chemical;
    (b-b) a second portion containing a second chemical, the second chemical separated from the first chemical by a separating mechanism.

12. The apparatus of claim 11 wherein the light is generated upon the breaking of the separating mechanism.

13. The apparatus of claim 9 wherein the mask comprises a transparent section that exposes the light to the portion of the skin.

14. The apparatus of claim 9 wherein the mask comprises an opaque section.

15. The apparatus of claim 9 wherein the mask is made from a flexible material.

16. The apparatus of claim 9 wherein the mask is at least one of a face mask and a body mask.

17. The apparatus of claim 9, wherein the light source further comprises an additional light source generating additional light having a wavelength between about 525 nm and about 575 nm.

18. The apparatus of claim 9 wherein the light source further comprises an additional light source generating additional light having a wavelength approximately between 630 nm and 690 nm.

19. The apparatus of claim 9 further comprising a plurality of light sources to generate the light by chemiluminescence at a plurality of times.

20. The apparatus of claim 9 wherein the mask further comprises at least one port through which at least one of a first chemical and a second chemical are delivered to the mask for generation of the light.

21. The apparatus of claim 9, wherein the source of at least one of a skin softener and a cleanser is at least one of a skin softener and a skin cleanser impregnated into at least a portion of a surface of the back side.

22. The apparatus of claim 9, wherein the light source is capable of generating light having a wavelength between about 525 nm and about 575 nm and a wavelength between about 630 nm and about 690 nm.

* * * * *